(12) United States Patent
Iaccino et al.

(10) Patent No.: US 7,772,447 B2
(45) Date of Patent: Aug. 10, 2010

(54) PRODUCTION OF LIQUID HYDROCARBONS FROM METHANE

(75) Inventors: Larry L. Iaccino, Seabrook, TX (US); Elizabeth L. Stavens, Seabrook, TX (US); Matthew J. Vincent, Baytown, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 716 days.

(21) Appl. No.: 11/792,357

(22) PCT Filed: Dec. 19, 2005

(86) PCT No.: PCT/US2005/045703

§ 371 (c)(1),
(2), (4) Date: Jun. 5, 2007

(87) PCT Pub. No.: WO2006/083409

PCT Pub. Date: Aug. 10, 2006

(65) Prior Publication Data

US 2008/0047872 A1    Feb. 28, 2008

Related U.S. Application Data

(60) Provisional application No. 60/639,066, filed on Dec. 22, 2004.

(51) Int. Cl.
C07C 2/76 (2006.01)
C07C 2/64 (2006.01)

(52) U.S. Cl. ............... 585/322; 585/323; 585/320; 585/407; 585/943

(58) Field of Classification Search ............... 585/322, 585/323, 320, 407, 943
See application file for complete search history.

(56) References Cited

U.S. PATENT DOCUMENTS

| 4,727,206 A | 2/1988 | Clayson et al. |
|---|---|---|
| 5,026,937 A | 6/1991 | Bricker |
| 5,336,825 A | 8/1994 | Choudhary et al. |
| 5,348,982 A | 9/1994 | Herbolzheimer et al. |
| 5,491,270 A | 2/1996 | Chin et al. |
| 5,936,135 A | 8/1999 | Choudhary et al. |
| 6,114,279 A | 9/2000 | Fukui et al. |

(Continued)

FOREIGN PATENT DOCUMENTS

RU    2 135 441    8/1999

OTHER PUBLICATIONS

Ma et al., "On the Induction Period of Methane Aromatization over Mo-Based Catalysts", Journal of Catalysis, 194, (2000), pp. 105-114.

(Continued)

*Primary Examiner*—Thuan Dinh Dang
(74) *Attorney, Agent, or Firm*—Andrew B. Griffis

(57) ABSTRACT

In a process for converting methane to liquid hydrocarbons, a feed containing methane is contacted with 0 dehydrocyclization catalyst under conditions effective to convert said methane to aromatic hydrocarbons, including benzene and/or naphthalene, and produce a first effluent stream comprising hydrogen and 0t least 5 wt % m>35 aromatic hydrocarbons than said feed. At least part the aromatic hydrocarbons from the first effluent stream is then reacted with hydrogen to produce a second effluent stream having a reduced benzene and/or naphthalene content compared with said first effluent stream.

38 Claims, 3 Drawing Sheets

U.S. PATENT DOCUMENTS

| | | |
|---|---|---|
| 6,239,057 B1 | 5/2001 | Ichikawa et al. |
| 6,426,442 B1 | 7/2002 | Ichikawa et al. |
| 6,552,243 B2 | 4/2003 | Allison et al. |
| 2002/0035305 A1 | 3/2002 | Ichikawa et al. |
| 2002/0112989 A1 | 8/2002 | Shih et al. |
| 2003/0144565 A1 | 7/2003 | Allison et al. |
| 2004/0015025 A1 | 1/2004 | Bellussi et al. |
| 2004/0097770 A1 | 5/2004 | Dakka et al. |

OTHER PUBLICATIONS

Liu et al., "Non-oxidative Dehydroaromatization of Methane over Ga-promoted Mo-HZSM-5-based Catalysts", Applied Catalysis A: General, 214, (2001), pp. 95-102.

Japan Chemical Week Incorporating Asia Report, "Benzene Synthesized Directly from Methane: Mitsubishi Chem", The Chemical Daily Co., Ltd., vol. 46, No. 2337, ISSN 0047-1755, Oct. 6, 2005.

US 7,772,447 B2

PRODUCTION OF LIQUID HYDROCARBONS FROM METHANE

CROSS REFERENCE TO RELATED APPLICATIONS

This application is a National Stage Application of International Application No. PCT/US2005/045703 filed Dec. 19, 2005, which claims the benefit of Provisional Application No. 60/639,066, filed Dec. 22, 2004, the entirety of which is incorporated be reference.

FIELD

This application describes a process for producing liquid hydrocarbons from methane and, in particular, from natural gas.

BACKGROUND

Transportable liquid hydrocarbons, such as cyclohexane and decalin, are important commodities for fuel and chemical use. Currently, liquid hydrocarbons are mostly frequently produced from crude oil-based feedstocks by a variety of processes. However, as the world supplies of crude oil feedstocks decrease, there is a growing need to find alternative sources of liquid hydrocarbons.

One possible alternative source of liquid hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, is a particularly attractive method of upgrading natural gas, providing the attendant technical difficulties can be overcome.

A large majority of the processes for converting methane to liquid hydrocarbons involve first conversion of the methane to synthesis gas, a blend of $H_2$ and CO. Production of synthesis gas is capital and energy intensive; therefore routes that do not require synthesis gas generation are preferred.

A number of alternative processes have been proposed for converting methane directly to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

Dehydroaromatization of methane via high-temperature reductive coupling has also been proposed as a route for upgrading methane into higher hydrocarbons, particularly ethylene, benzene and naphthalene. Thus, for example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

U.S. Pat. No. 5,026,937 discloses a process for the aromatization of methane which comprises the steps of passing a feed stream, which comprises over 0.5 mole percent hydrogen and 50 mole percent methane, into a reaction zone having at least one bed of solid catalyst comprising ZSM-5 and phosphorous-containing alumina at conversion conditions which include a temperature of 550° C. to 750° C., a pressure less than 10 atmospheres absolute (1000 kPaa) and a gas hourly space velocity of 400 to 7,500 $hr^{-1}$. The product effluent is said to include methane, hydrogen, at least 3 mole % $C_2$ hydrocarbons and at least 5 mole % $C_6$-$C_8$ aromatic hydrocarbons. After condensation to remove the $C_4$+ fraction, cryogenic techniques are proposed to separate the hydrogen and light hydrocarbons (methane, ethane, ethylene, etc.) in the product effluent.

U.S. Pat. No. 5,936,135 discloses a low temperature, non-oxidative process for the conversion of a lower alkane, such as methane or ethane, to aromatic hydrocarbons. In this process, the lower alkane is mixed with a higher olefin or paraffin, such as propylene or butene, and the mixture is contacted with a pretreated bifunctional pentasil zeolite catalyst, such as GaZSM-5, at a temperature of 300° C. to 600° C., a gas hourly space velocity of 1000 to 100000 $cm^3g^{-1}hr^{-1}$ and a pressure of 1 to 5 atmosphere (100 to 500 kPa). Pretreatment of the catalyst involves contacting the catalyst with a mixture of hydrogen and steam at a temperature 400° C. to 800° C., a pressure of 1 to 5 atmosphere (100 to 500 kPa) and a gas hourly space velocity of at least 500 $cm^3g^{-1}hr^{-1}$ for a period of at least 0.5 hour and then contacting the catalyst with air or oxygen at a temperature of 400° C. to 800° C., a gas hourly space velocity of at least 200 $cm^3g^{-1}hr^{-1}$ and a pressure of 1 to 5 atmosphere (100 to 500 kPa) for a period of at least 0.2 hour.

U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. The addition of CO or $CO_2$ to the feed is said to increase the yield of benzene and the stability of the catalyst.

U.S. Pat. No. 6,552,243 discloses a process for the non-oxidative aromatization of methane, in which a catalyst composition comprising a metal-loaded, crystalline aluminosilicate molecular sieve is initially activated by treatment with a mixture of hydrogen and a $C_2$ to $C_4$ alkane, preferably butane, and then the activated catalyst is contacted with a feed stream comprising at least 40 mole percent methane at a temperature of 600° C. to 800° C., a pressure of less than 5 atmosphere absolute (500 kPaa), and a weight hourly space velocity (WHSV) of 0.1 to 10 $hr^{-1}$.

Russian Patent No. 2,135,441 discloses a process for converting methane to heavier hydrocarbons, in which the methane is mixed with at least 5 wt % of a $C_3$+ hydrocarbon, such as benzene, and then contacted in a multi-stage reactor system with a catalyst comprising metallic platinum having a degree of oxidation greater than zero at a methane partial pressure of at least 0.05 MPa and a temperature of at least 440° C. Hydrogen generated in the process may be contacted with oxides of carbon to generate additional methane that, after removal of the co-produced water, can be added to the methane feed. The products of the methane conversion are a $C_2$-$C_4$ gaseous phase and a $C_5$+ liquid phase but, according the Examples, there is little (less than 5 wt %) or no net increase in aromatic rings as compared with the feed.

Existing proposals for the conversion of methane to aromatic hydrocarbons suffer from a variety of problems that have limited their commercial potential. Oxidative coupling methods generally involve highly exothermic and potentially hazardous methane combustion reactions, frequently require expensive oxygen generation facilities and produce large quantities of environmentally sensitive carbon oxides. On the other hand, existing reductive coupling techniques frequently have low selectivity to aromatics and may require expensive co-feeds to improve conversion and/or aromatics selectivity. Moreover, any reductive coupling process generates large quantities of hydrogen and so, for economic viability, requires a route for effective utilization of the hydrogen by-product. Since natural gas fields are frequently at remote locations, effective hydrogen utilization can present a substantial challenge.

An additional limitation of these technologies is that they tend to produce predominately benzene and naphthalene as products. While benzene has potential value as a chemical feedstock it has a limited chemical market and is not viable as a fuel source due to health and environmental issues. Naphthalene has an even more limited chemicals market and is more challenging for use as a fuel due to health and environmental issues plus a melting point higher than ambient temperature.

A particular difficulty in using natural gas as a liquid hydrocarbon source concerns the fact that many natural gas fields around the world contain large quantities, sometimes in excess of 50%, of carbon dioxide. Not only is carbon dioxide a target of increasing governmental regulation because of its potential contribution to global climate change, but also any process which requires separation and disposal of large quantities of carbon dioxide from natural gas is likely to be economically prohibitive. In fact, some natural gas fields have such high carbon dioxide levels as to be currently considered economically unrecoverable.

There is therefore a need for an improved process for converting methane to liquid hydrocarbons, particularly where the methane is present in a natural gas stream containing large quantities of carbon dioxide.

SUMMARY

In one aspect, this application describes a process for converting methane to higher hydrocarbons, the process comprising:
(a) contacting a feed containing methane and at least one of $H_2$, $H_2O$, CO and $CO_2$ with a dehydrocyclization catalyst under conditions effective to convert said methane to aromatic hydrocarbons, including benzene and/or naphthalene, and produce a first effluent stream comprising aromatic hydrocarbons and hydrogen, wherein said first effluent stream comprises at least 5 wt % more aromatic hydrocarbons than said feed; and
(b) reacting at least part of said aromatic hydrocarbons from said first effluent stream with hydrogen to produce a second effluent stream having a reduced benzene and/or naphthalene content compared with said first effluent stream.

Conveniently, said feed in (a) contains less than 5 wt % of $C_3$+ hydrocarbons. As used herein, the term "$C_3$+ hydrocarbons" means hydrocarbons having 4 or more carbon atoms.

Conveniently, said conditions in (a) are non-oxidizing conditions. By "non-oxidizing" is meant that oxidizing agents (such as, $O_2$, $NO_x$ and metal oxides which can release oxygen to oxidize methane to $CO_x$) are present at less than 5%, preferably at less then 1%, most preferably at less than 0.1%, of the amount required for stoichiometric oxidation of the methane.

Typically said conditions in (a) include a temperature of 400° C. to 200° C., such as 500° C. to 975° C., for example 600° C. to 950° C.

Conveniently, said reacting (b) converts at least part of the benzene and/or naphthalene in said first effluent stream to one or more of cyclohexane, cyclohexene, dihydronaphthalene (benzylcyclohexene), tetrahydronaphthalene(tetralin), hexahydronaphthalene(dicyclohexene), octahydronaphthalene, and decahydronaphthalene(decalin).

Conveniently, said reacting (b) hydrogenates and hydrocracks at least a portion of the naphthalene in said first effluent stream to produce alkylated one ring aromatic species such as ethylbenzene, xylenes, cumene, tri-methylbenzene, butylbenzene, diethylbenzene, methylethylbenzene and other typical isomers.

In one embodiment, said reacting (b) hydrocracks at least part of the benzene and/or naphthalene in said first effluent stream to normal and/or isoparaffins.

Conveniently, at least part of the benzene and/or naphthalene in said first effluent stream can be further reacted with cyclohexene, conveniently formed by said reacting (c), to respectively form cyclohexyl benzene and/or cyclohexyl naphthalene.

Conveniently, the process also comprises separating at least one aromatic hydrocarbon, typically benzene and/or naphthalene, from said first effluent stream. Before or after said separating, the aromatic compounds in said first effluent stream can be alkylated with an alkylating agent. In one embodiment, the alkylating agent is ethylene produced in said contacting (a). In another embodiment, the alkylating agent comprises carbon monoxide and hydrogen or a reaction product thereof, wherein the carbon monoxide is produced by said reacting (b).

In a further aspect, the this application describes a process for converting methane to higher hydrocarbons, the process comprising:
(a) contacting a feed containing methane and CO and/or $CO_2$ with a dehydrocyclization catalyst under non-oxidizing conditions effective to convert said methane to aromatic hydrocarbons, including benzene and/or naphthalene, and produce a first effluent stream comprising aromatic hydrocarbons and hydrogen, wherein said first effluent stream comprises at least 5 wt % more aromatic hydrocarbons than said feed;
(b) reacting at least part of said aromatic hydrocarbons from said first effluent stream with at least part of the hydrogen from said first effluent stream to produce a second effluent stream having a reduced benzene and/or naphthalene content compared with said first effluent stream;
(c) reacting at least part of the hydrogen from said second effluent stream with an oxygen containing species to produce a third effluent stream comprising water and hydrocarbon; and
(d) recycling at least part of the hydrocarbon in said third effluent stream to said contacting (a).

It is to be appreciated that references herein to the first effluent stream comprising at least 5 wt % more aromatic rings than the feed is intended to mean that the total number of aromatic rings in the first effluent stream should exceed the total number of aromatic rings in the feed by at least 5 wt %. For example, if the feed contains 1 wt % of aromatic rings, the first effluent stream will contain at least 6 wt % of aromatic rings. Changes in substituents on any aromatic rings between the feed and the first effluent stream are not included in this calculation.

DETAILED DESCRIPTION OF THE EMBODIMENTS

Figure 1:
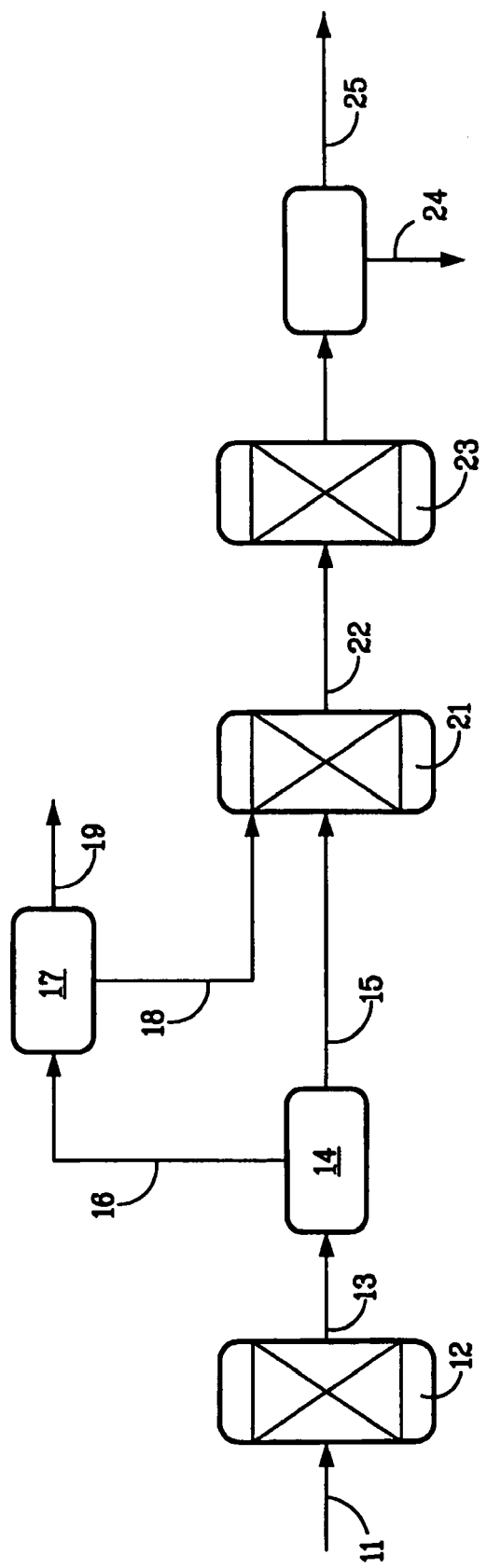
FIG. 1 is a flow diagram of a process for converting methane to higher hydrocarbons according to a first example of the invention.

This application describes a process for converting methane to liquid hydrocarbons by subjecting a feed containing methane, typically together with at least one of $H_2$, $H_2O$, CO and $CO_2$, to a dehydrocyclization step under conditions effective to convert methane to aromatic hydrocarbons and produce a first effluent stream comprising aromatic hydrocarbons and hydrogen, wherein the first effluent stream comprises at least 5 wt % more aromatic hydrocarbons than the feed.

The first effluent stream is then subjected to a hydrogenation step in which at least part of the benzene or naphthalene from said first effluent stream is reacted with hydrogen, preferably at least part of the hydrogen from said first effluent stream, to produce a second effluent stream having a reduced benzene or naphthalene content compared with the first effluent stream. At least one liquid hydrocarbon fraction, such as cyclohexane, cyclohexene, dihydronaphthalene(benzylcyclohexene), tetrahydronaphthalene(tetralin), hexahydronaphthalene(dicyclohexene), octahydronaphthalene, or decahydronaphthalene(decalin), is recovered from the second effluent stream. If desired, the first effluent stream can be subjected to an aromatics alkylation step prior to or after hydrogenation of one or more aromatic hydrocarbon fractions.

Feedstock

Any methane-containing feedstock can be used in the process of the invention but in general the present process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can of course be converted to desired aromatics products in the dehydrocyclization step. In addition, as will be discussed below, carbon dioxide can also be converted to useful aromatics products either directly in the dehydrocyclization step or indirectly through conversion to methane and/or other hydrocarbons in the hydrogen rejection step.

Nitrogen and/or sulfur impurities are also typically present in methane-containing streams and are preferably removed, or reduced to low levels, prior to use of the streams in the process of the invention. In general, the feed to the dehydrocyclization step should contain less than 100 ppm, for example less than 10 ppm, such as less than 1 ppm each of nitrogen and sulfur compounds.

In addition to methane, the feed to the dehydrocyclization step preferably contains at least one of hydrogen, water, carbon monoxide and carbon dioxide in order to assist in coke mitigation. These additives can be introduced as separate co-feeds or can be present in the methane stream, such as, for example, where the methane stream is derived from natural gas containing carbon dioxide. Other suitable sources of carbon dioxide include flue gases, LNG plants, hydrogen plants, ammonia plants, glycol plants and phthalic anhydride plants.

In one embodiment, the feed to the dehydrocyclization step contains carbon dioxide and comprises 90 to 99.9 mol %, such as 97 to 99 mol % methane and 0.1 to 10 mol %, such as 1 to 3 mol %, $CO_2$. In another embodiment, the feed to the dehydrocyclization step contains carbon monoxide and comprises 80 to 99.9 mol %, such as 94 to 99 mol %, methane and 0.1 to 20 mol %, such as 1 to 6 mol %, CO. In a third embodiment, the feed to the dehydrocyclization step contains steam and comprises 90 to 99.9 mol %, such as 97 to 99 mol %, methane and 0.1 to 10 mol %, such as 1 to 3 mol %, steam. In a fourth embodiment, the feed to the dehydrocyclization step contains hydrogen and comprises 80 to 99.9 mol % hydrocarbon, such as 95 to 99 mol %, methane and 0.1 to 20 mol %, such as 1 to 5 mol %, hydrogen.

The feed to the dehydrocyclization step can also contain higher hydrocarbons than methane, including aromatic hydrocarbons. Such higher hydrocarbons can be added as separate co-feeds or can be present in the methane stream, such as, for example, when ethane is present in a natural gas feed. In general, however, the feed to the dehydrocyclization step contains less than 5 wt %, such as less than 3 wt %, of $C_3$+ hydrocarbons.

Dehydrocyclization

In the dehydrocyclization step of the present process, the methane containing feed is contacted with a dehydrocyclization catalyst under conditions, normally non-oxidizing conditions and preferably reducing conditions, effective to convert the methane to higher hydrocarbons, including benzene and naphthalene. The principal reactions involved are as follows:

$$2CH_4 \leftrightarrow C_2H_4 + 2H_2 \qquad \text{(Reaction 1)}$$

$$6CH_4 \leftrightarrow C_6H_6 + 9H_2 \qquad \text{(Reaction 2)}$$

$$10CH_4 \leftrightarrow C_{10}H_8 + 16H_2 \qquad \text{(Reaction 3)}$$

Carbon monoxide and/or dioxide that may be present in the feed improves catalyst activity and stability by facilitating reactions such as:

$$CO_2 + \text{coke} \rightarrow 2CO \qquad \text{(Reaction 4)}$$

but negatively impacts equilibrium by allowing competing net reactions, such as;

$$CO_2 + CH_4 \leftrightarrow CO + 2H_2 \qquad \text{(Reaction 5).}$$

Any dehydrocyclization catalyst effective to convert methane to aromatics can be used in the process of the invention, although generally the catalyst will include a metal component, particularly a transition metal or compound thereof, on an inorganic support. Conveniently, the metal component is present in an amount between 0.1% and 20%, such as between 1% and 10%, by weight of the total catalyst.

Suitable metal components for the catalyst include calcium, magnesium, barium, yttrrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth and transuranium metals. Such metal components may be present in elemental form or as metal compounds, such as oxides, carbides, nitrides and/or phosphides, and may be employed alone or in combination. Platinum and Osmium can also be used as one of the metal component but, in general, are not preferred.

The inorganic support may be either amorphous or crystalline and an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous or mesoporous crystalline material. Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50 and SBA-15.

Examples of preferred catalysts include molybdenum, tungsten, rhenium and compounds and combinations thereof on ZSM-5, silica or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

The dehydrocyclization step can be conducted over a wide range of conditions including a temperature of 400° C. to 1200° C., such as 500° C. to 975° C., for example 600° C. to 950° C., a pressure of 1 kPa to 1000 kPa, such as 10 to 500 kPa, for example 50 kPa to 200 kPa and a weight hourly space velocity of 0.01 to 1000 hr$^{-1}$, such as 0.1 to 500 hr$^{-1}$, for example 1 to 20 hr$^{-1}$. Conveniently, the dehydrocyclization step is conducted in the absence of $O_2$.

The dehydrocyclization step can be conducted in one or more fixed beds, moving beds or fluidized bed reactors, with catalyst regeneration being conducted in-situ or ex-situ with air, oxygen, carbon dioxide, carbon monoxide, water, hydrogen or combinations thereof.

The dehydrocyclization reaction is endothermic and, hence where the reaction is conducted in a plurality of stages, it may be necessary to employ interstage heating to return the feed to the required reaction temperature. The fuel required to provide the interstage heating is conveniently obtained by removing and combusting a sidestream from the dehydrocyclization effluent, after separation of the aromatic components. In addition, where the reaction occurs in the presence of a moving bed of catalyst, a portion or all of the heat may be supplied by withdrawing a portion of the catalyst from the bed, heating the catalyst by, for example, combustion of coke on the catalyst, and then returning the heated catalyst to the moving catalyst bed.

The major components of the effluent from the dehydrocyclization step are hydrogen, benzene, naphthalene, carbon monoxide, ethylene, and unreacted methane. Typically, the effluent contains at least 5 wt %, such as at least 10 wt %, for example at least 20 wt % more aromatic hydrocarbons than the feed.

Aromatic Product Recovery/Treatment

The benzene and naphthalene can be separated from the dehydrocyclization effluent, typically by solvent extraction followed by fractionation, and then sold directly as commodity chemicals. In addition, before or after separation from the dehydrocyclization effluent, some or all of the benzene and/or naphthalene can be alkylated to produce, for example, toluene, xylenes and alkyl naphthalenes. In accordance with the invention, however, at least part of the aromatic components of the dehydrocyclization effluent is subjected to hydrogenation to generate useful liquid products such as cyclohexane, cyclohexene, dihydronaphthalene(benzylcyclohexene), tetrahydronaphthalene(tetralin), hexahydronaphthalene(dicyclohexene), octahydronaphthalene and/or decahydronaphthalene(decalin). These products can be employed as fuels and chemical intermediates and, in the case of tetralin and decalin, can be used as the solvent for extracting the aromatic components from the dehydrocyclization effluent.

Where the dehydrocyclization process is conducted at a remote location, hydrogenation of the aromatic components can also be used as an effective method for converting some of the hydrogen by-product into liquid from, namely the liquid products of the hydrogenation process, to facilitate transportation of the hydrogen to a location where it will have more value. In this case, after transportation of the liquid product it may be economically viable to reconvert the liquid product back to the original aromatic components and hydrogen.

Aromatics Hydrogenation

Conveniently, at least part of the benzene and/or naphthalene is reacted with hydrogen from the first effluent stream to produce one or more of cyclohexane, cyclohexene, dihydronaphthalene(benzylcyclohexene), tetrahydronaphthalene (tetralin), hexahydronaphthalene(dicyclohexene), octahydronaphthalene, and decahydronaphthalene(decalin). Exemplary reactions are the production of cyclohexene as follows:

$$C_6H_6 + 2H_2 \rightarrow C_6H_{10};$$

the production of dihydronaphthalene as follows:

$$C_{10}H_8 + H_2 \rightarrow C_{10}H_{10};$$

the production of tetrahydronaphthalene as follows:

$$C_{10}H_8 + 2H_2 \rightarrow C_{10}H_{12};$$

the production of hexahydronaphthalene as follows: and $$C_{10}H_8 + 3H_2 \rightarrow C_{10}H_{14};$$

the production of decahydronaphthalene as follows:

$$C_{10}H_8 + 5H_2 \rightarrow C_{10}H_{18}.$$

A portion of the naphthalene may also be subjected to hydrogenation of one ring followed by hydrocracking of the ring to produce various alkylated one ring aromatic species such as ethylbenzene, xylenes, cumene, tri-methylbenzene, butylbenzene, diethylbenzene, methylethylbenzene and other typical isomers. Although typically of less value, the benzene and/or naphthalene can also be hydrocracked to a distribution of carbon numbers and isomers of normal and isoparaffins.

Conveniently, at least part of the benzene and/or naphthalene can be further reacted with produced cyclohexene to respectively form cyclohexyl benzene or cyclohexyl naphthalene.

There are several general reasons why it is advantageous to perform hydrogenation of the benzene and naphthalene:

Consumption of a portion of the coproduced hydrogen reduces the need for other methods of utilizing the hydrogen—remote, low value hydrogen is converted to chemically bound, transportable hydrogen Fuels with higher hydrogen content are preferred as lower $CO_2$ emissions per energy content are possible Very low sulfur fuels are produced which are desirable for both conventional usages as well as fuel cell applications where sulfur is particularly detrimental Benzene is converted to materials with:
  Reduced health and environment issues
    Cyclohexane has high value as feedstock for polymer production
    Cyclohexene can be used directly as a monomer for polymer products or can be easily reacted to produce materials such as cyclohexanone or cyclohexylbenzene Naphthalene is converted to materials with:
  Reduced health and environment issues
    Potential to solidify at ambient temperature is eliminated
    Cyclohexane has high value as feedstock for polymer production
    Dihydronaphthalene(benzylcyclohexene), hexahydronaphthalene(dicyclohexene), octahydronaphthalene can be used directly as a monomer for polymer products or can be easily reacted to produce materials such as benzylcyclohexanone or dicyclohexanone
    Decalin can have high value as a jet fuel, particularly as a high density fuel for military aircraft
    hydrocracked to a distribution of carbon numbers and isomers of normal and isoparaffins can yield low aromatic, low sulfur diesel and jet fuel
    hydrogenation of one ring followed by hydrocracking of the ring to produce various alkylated one ring aromatic species, such as ethylbenzene, xylenes, cumene, tri-methylbenzene, butylbenzene, diethylbenzene, methylethylbenzene and other typical isomers, yields a product stream that can be used for chemicals recovery or production of high octane, low sulfur internal combustion engine fuel The hydrogenation is conveniently, but not necessarily, conducted after separation of the aromatic components from the dehydrocyclization effluent and conveniently employs part of the hydrogen generated by the dehydrocyclization reaction. If the feed contains nitrogen and/or sulfur impurities, it may be desirable to treat the hydrogen generated by the dehydrocyclization reaction to reduce the levels of sulfur and nitrogen compounds in the hydrogen before the hydrogen is used to hydrogenate the aromatic components from the dehydrocyclization effluent. It may also be desirable to remove at least a portion of the unreacted methane and other light hydrocarbons from the hydrogen stream prior to use. Hydrogen content of the stream may also be improved by steam reforming of the stream prior to use in hydrogenation. The hydrogen stream after use for hydrogenation may be enriched in $C_1$-$C_5$ paraffins which are suitable for recycle to the dehydrocyclization reactor.

Suitable aromatic hydrogenation processes are well known in the art and typically employ a catalyst comprising Ni, Pd, Pt, Ni/Mo or sulfided Ni/Mo supported on alumina or silica support or other high surface area inorganic support. Suitable operating conditions for the hydrogenation process include a temperature of 300 to 1,000° F. (150 to 540° C.), such as 500 to 700° F. (260 to 370° C.), a pressure of t 50 to 2,000 psig (445 to 13890 kPa), such as 100 to 500 psig (790 to 3550 kPa) and a WHSV of 0.5 to 50 hr$^{-1}$, such as 2 to 10 hr$^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta or other high surface area inorganic support. Suitable operating conditions for low pressure hydrocracking include a temperature of 300 to 1,000° F. (150 to 540° C.), such as 500 to 700° F. (260 to 370° C.), a pressure of 50 to 2,000 psig (445 to 13890 kPa), such as 100 to 500 psig (790 to 3550 kPa) and a WHSV of 0.5 to 50 hr$^{-1}$, such as 2 to 10 hr$^{-1}$.

An alternative hydrogenation process involves hydrocracking of the benzene or naphthalene component to produce normal or branched paraffins over a catalyst such as Group VIII metals, with Pt and Ir being preferred, supported on an amorphous aluminosilicate or a zeolite, such as zeolite X, zeolite Y or zeolite beta or other high surface area inorganic support. Suitable operating conditions for low pressure hydrocracking include a temperature of 300 to 1,000° F. (150 to 540° C.), such as 500 to 700° F. (260 to 370° C.), a pressure of 50 to 2,000 psig (445 to 13890 kPa), such as 100 to 500 psig (790 to 3550 kPa) and a WHSV of 0.5 to 50 hr$^{-1}$, such as 2 to 10 hr$^{-1}$.

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e., those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from 650 to 900° F. (343 to 482° C.), a pressure of atmospheric to 3000 psig (100 to 20,800 kPa), a WHSV based on ethylene of from 0.5 to 2.0 hr$^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from 0.1 to 20 hr$^{-1}$ and a mole ratio of benzene to ethylene of from 1:1 to 30:1.

Preferably, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a medium pore zeolite, such as ZSM-5, Beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of 0.1-15 sec$^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to or after separation of the aromatic components, can be fed to a reverse shift reactor and reacted with the carbon dioxide-containing feed under conditions to increase the carbon monoxide content of the effluent by reactions, such as Reaction 5 and the following reverse water gas shift reaction:

$CO_2 + H_2 \leftrightarrow CO + H_2O$ <span style="float:right">(Reaction 6)</span>

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn and Cu on alumina, silica or titania, and is operated under conditions including a temperature of 500° C. to 1200° C., such as 600° C. to 1000° C., for example 700° C. to 950° C. and a pressure of 1 kPa to 10,000 kPa, such as 2,000 kPa to 10,000 kPa, for example 3000 kPa to 5,000 kPa. Gas hourly space velocities may vary depending upon the type of process used, but generally the gas hourly space velocity of flow of gas through the catalyst bed is in the range of 50 hr$^{-1}$ to 50,000 hr$^{-1}$, such as 250 hr$^{-1}$ to 25,000 hr$^{-1}$, more preferably 500 hr$^{-1}$ to 10,000 hr$^{-1}$.

The effluent from the reverse shift reactor can then be fed to an alkylation reactor operating under conditions to cause reactions such as the following to occur:

$CO + 2H_2 \leftrightarrow CH_3OH$ <span style="float:right">(Reaction 7)</span>

$CH_3OH + C_6H_6 \rightarrow toluene + 2H_2O$ <span style="float:right">(Reaction 8)</span>

$2CH_3OH + C_6H_6 \rightarrow xylenes + 2H_2O$ <span style="float:right">(Reaction 9)</span>

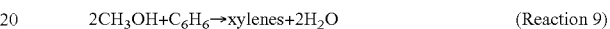

Suitable conditions for such an alkylation reactor would include a temperature of 100 to 700° C., a pressure of 1 to 300 atmospheres (100 to 30,000 kPa), and a WHSV for the aromatic hydrocarbon of 0.01 to 100 hr$^{-1}$. A suitable catalyst would comprise a molecular sieve having a constraint index of 1 to 12, such as ZSM-5, typically together with one or metals or metal oxides, such as copper, chromium and/or zinc oxide.

Preferably, where the alkylation catalyst includes a molecular sieve, the latter is modified to change its diffusion characteristics such that the predominant xylene isomer produced by Reaction 9 is paraxylene. Suitable means of diffusion modification include ex-situ or in-situ deposition of coke, silicon, and/or metal oxides on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit and preferably a selective toluene disproportionation unit for the preparation of additional p-xylene.

Hydrogen Rejection

Hydrogen is a major component of the dehydrocyclization effluent and, although part of this hydrogen is used in the hydrogenation of the aromatic products and possibly in the optional alkylation step, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species to produce water and a second effluent stream having a reduced hydrogen content compared with the first (dehydrocyclization) effluent stream.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \quad \text{(Reaction 10)}$$

$$2CO_2 + 7H_2 \leftrightarrow C_2H_6 + 4H_2O \quad \text{(Reaction 11)}$$

The carbon dioxide employed is conveniently part of a natural gas stream and preferably the same natural gas stream used as the feed to the dehydrocyclization step. Where the carbon dioxide is part of a methane-containing stream, the $CO_2$:$CH_4$ of the stream is conveniently maintained between 1:1 and 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2$:$CO_2$ molar ratio close to the stoichiometric proportions required for the desired Reaction 10 or Reaction 11, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of 100° C. to 900° C., such as 150° C. to 500° C., for example 200° C. to 400° C., a pressure of 200 kPa to 20,000 kPa, such as 500 to 5000 kPa and a weight hourly space velocity of 0.1 to 10,000 hr$^{-1}$, such as 1 to 1,000 hr$^{-1}$. $CO_2$ conversion levels are typically between 20 and 100% and preferably greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2$:$CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of 0.5:1 to 4:1, preferably 1.5:1 to 2.5:1, at a temperature of 175° C. to 400° C., preferably 180° C. to 240° C. and a pressure of 1 to 100 bar (100 to 10,000 kPa), preferably 10 to 40 bar (1,000 to 4,000 kPa), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, preferably cobalt, with rhenium or zirconium as a promoter, preferably cobalt and rhenium supported on silica or titania, preferably titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$— ZnO and ZSM-5 Catalysts for the Transformation of Syngas into Liquid Hydrocarbons* by Jose Erena; Ind. Eng. Chem Res. 1998, 37, 1211-1219, incorporated herein by reference.

The Fischer-Tropsch liquids, i.e., $C_5$+, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to the Fischer-Tropsch reaction whereby the carbon dioxide is converted to carbon monoxide by the reverse water gas shift reaction.

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides (CO+$CO_2$) in the range of from 0.5:1 to 20:1, preferably in the range of from 2:1 to 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from 150° C. to 450° C., such as from 175° C. to 350° C., for example from 200° C. to 300° C. Suitable pressures are in the range of from 1,500 kPa to 12,500 kPa, such as from 2,000 kPa to 10,000 kPa, for example 2,500 kPa to 7,500 kPa. Gas hourly space velocities vary depending upon the type of process that is used, but generally the gas hourly space velocity of flow of gas through the catalyst bed is in the range of from 50 $hr^{-1}$ to 50,000 $hr^{-1}$, such as from 250 $hr^{-1}$ to 25,000 $hr^{-1}$, more preferably from 500 $hr^{-1}$ to 10,000 $hr^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of:

i) at least one metal from Group 3 and at least one metal from Groups 4-15 of the Periodic Table of the Elements;

ii) at least one metal from Groups 5-15 of the Periodic Table of the Elements, and at least one metal from at least one of Groups 1, 2, and 4 of the Periodic Table of the Elements;

iii) at least one metal from Groups 1-2, at least one metal from Group 3, and at least one metal from Groups 4-15 of the Periodic Table of the Elements; and iv) two or more metals from Groups 4-15 of the Periodic Table of the Elements and (b) at least one of oxygen and sulfur, wherein the at least one of oxygen and sulfur is chemically bound both within and between the metals.

The selective hydrogen combustion reaction of the present invention is generally conducted at a temperature in the range of from 300° C. to 850° C. and a pressure in the range of from 1 atm to 20 atm (100 to 2000 kPa).

The invention will now be more particularly described with reference to the following Examples and the accompanying drawings.

EXAMPLE 1

In a first example of the invention that is illustrated schematically in FIG. 1, a feed 11 comprising 100 kg of methane is fed to a dehydrocyclization reactor 12 that contains a catalyst comprising 3 wt % Mo on HZSM-5 (silica to alumina molar ratio of 25) and is operated at a temperature of about 800° C., a WHSV of 1 and a pressure of 20 psia (138 kPa). The effluent 13 from the dehydrocyclization reactor 12 is made up of an aromatic component comprising 10.78 kg of benzene and 2.45 kg of naphthalene and a fuel gas component comprising 79.62 kg of unreacted methane, 4.01 kg of hydrogen and 0.85 kg of ethylene.

The effluent 13 is fed to a first separator 14, where the effluent is separated, conveniently by solvent extraction, into the aromatic component 15 and the fuel gas component 16. The fuel gas component is then fed to a second separator 17, where a hydrogen stream 18 comprising 1.05 kg of hydrogen is removed from the component 16 to generate a fuel gas product 19 comprising 79.62 kg of unreacted methane, 2.96 kg of hydrogen and 0.85 kg of ethylene. The hydrogen stream 18 and the aromatic component 15 are then fed to a hydrogenation reactor 21 where the aromatic component is hydrogenated to produce a liquid hydrocarbon product 22 comprising 11.6 kg of cyclohexane and 2.7 kg of decalin.

The liquid hydrocarbon product 22 can be recovered for use as, for example, a fuel or can be transported to a more desirable location, for example a chemical plant, where the product can be fed to a dehydrogenation reactor 23 for conversion and separation back to an aromatic product stream 24 comprising 10.78 kg of benzene and 2.45 kg of naphthalene and a hydrogen product stream 25 comprising 1.05 kg of hydrogen.

EXAMPLE 2

Figure 2:
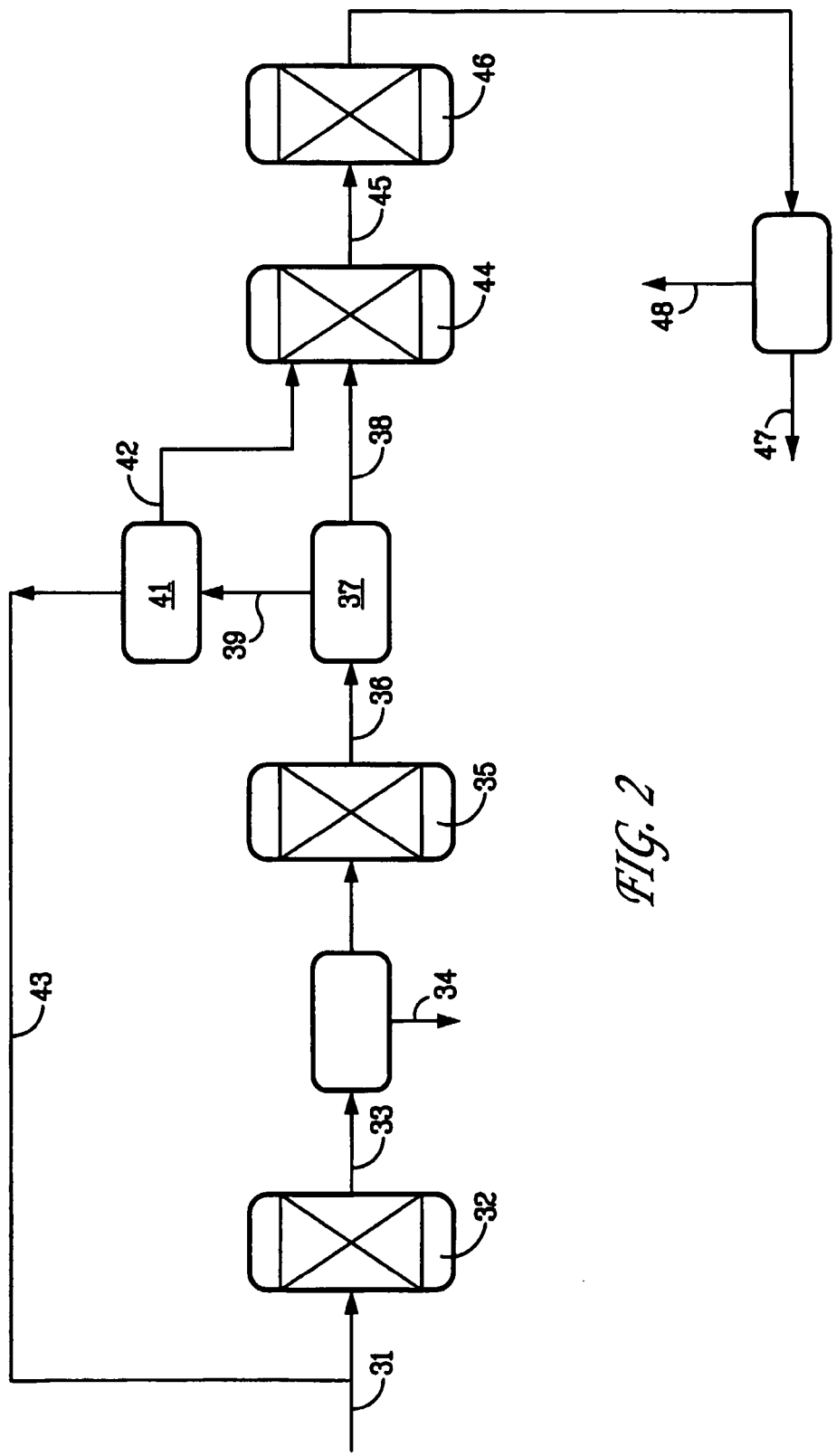
FIG. 2 is a flow diagram of a process for converting methane to higher hydrocarbons according to a second example of the invention.

In a second example of the invention illustrated schematically in FIG. 2, the feed 31 comprises 114 kg of carbon dioxide in addition to 100 kg of methane and is initially fed to a methanation reactor 32 that contains a Cu/Zn catalyst and is operated at a temperature of 300° C., a WHSV of 1 and a pressure of 350 psia (2413 kPa). The effluent stream 33 from the methanation reactor 32 is fed to a condenser 34, where 94 kg water is recovered, and then the remaining effluent is fed to a dehydrocyclization reactor 35 that contains a catalyst comprising 3 wt % Mo on HZSM-5 (silica to alumina molar ratio of 25) and is operated at a temperature of about 800° C., a WHSV of 1 and a pressure of 20 psia (138 kPa). The effluent 36 from the dehydrocyclization reactor 35 is made up of an aromatic component comprising 78.8 kg of benzene and 17.2 kg of naphthalene and a fuel gas component comprising unreacted methane, hydrogen and ethylene.

The effluent 36 is fed to a first separator 37, where the effluent is separated, conveniently by solvent extraction, into the aromatic component 38 and the light gas component 39. The light gas component is then fed to a second separator 41, where a hydrogen stream 42 is removed from light gas component and the remainder of the light gas is recycled as stream 43 to the methanation reactor 32. The hydrogen stream 42 and the aromatic component 38 are then fed to a hydrogenation reactor 44 where the aromatic component is hydrogenated to produce a liquid hydrocarbon product 45 comprising 84.9 kg of cyclohexane and 18.7 kg of decalin.

As in Example 1, the liquid hydrocarbon product 45 can be recovered for use as, for example, a fuel or can be transported to a more desirable location, for example a chemical plant, where the product can be fed to a dehydrogenation reactor 46 for conversion and separation back to an aromatic product stream 47 comprising 78.8 kg of benzene and 17.2 kg of naphthalene and a hydrogen product stream 48.

EXAMPLE 3 (COMPARATIVE)

In this comparative example, the process of Example 2 is repeated but without the aromatic component 38 being hydrogenated and with all the light gas component 39 being recycled to the methanation reactor 32. In this case, using a feed comprising 100 kg of methane and 114 kg of carbon dioxide, 149 kg water is recovered in the condenser 34 and the aromatic component 38 comprises 93 kg of benzene and 22 kg of naphthalene.

EXAMPLE 4

Figure 3:
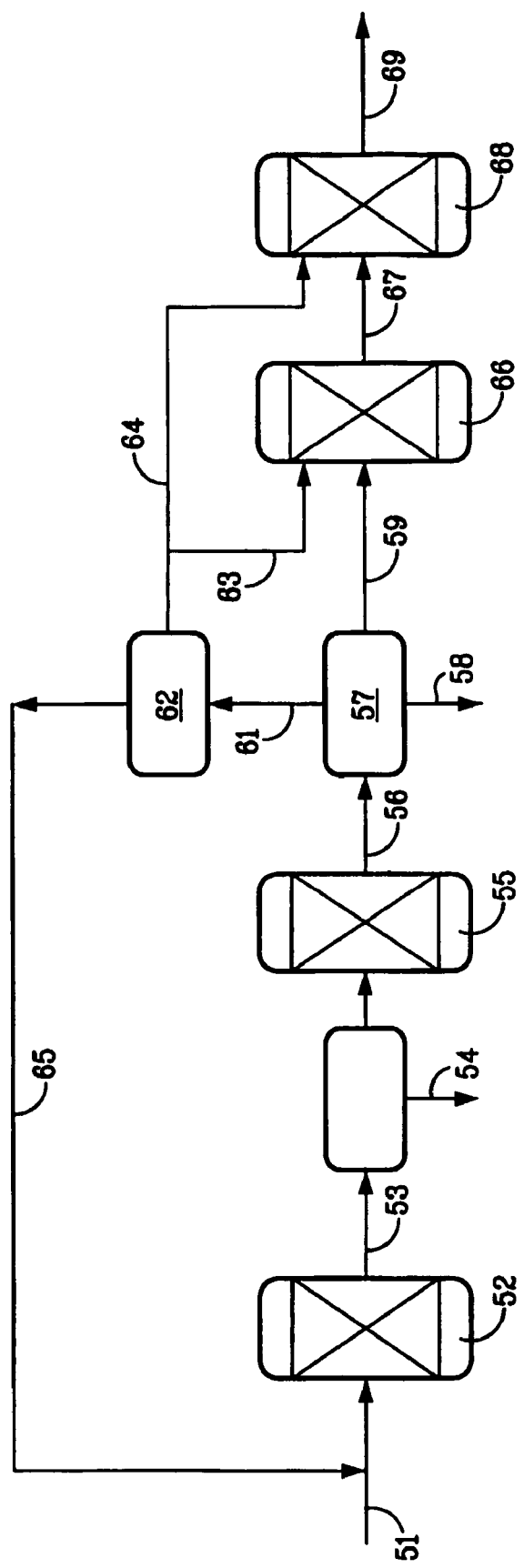
FIG. 3 is a flow diagram of a process for converting methane to higher hydrocarbons according to a fourth example of the invention.

In a fourth example of the invention illustrated schematically in FIG. 3, the feed 51 comprises 100 kg of methane and 70 kg of carbon dioxide and is initially to a methanation reactor 52 that contains a Cu/Zn catalyst and is operated at a temperature of 300° C., a WHSV of 1 and a pressure of 350 psia (2413 kPa). The effluent stream 53 from the methanation reactor 52 is fed to a condenser 54, where 57 kg water is recovered, and then the remaining effluent is fed to a dehydrocyclization reactor 55 that contains a catalyst comprising 3 wt % Mo on HZSM-5 (silica to alumina molar ratio of 25) and is operated at a temperature of about 800° C., a WHSV of 1 and a pressure of 20 psia (138 kPa). The effluent 56 from the dehydrocyclization reactor is made up of an aromatic component comprising 69.8 kg of benzene and 15.9 kg of naphthalene and a fuel gas component comprising unreacted methane, hydrogen and ethylene.

The effluent 56 is fed to a first separator 57, where the effluent is separated into a benzene product stream 58, which is recovered, a naphthalene stream 59 and the light gas component 61. The light gas component 61 is then fed to a second separator 62, where first and second hydrogen streams 63, 64 respectively are removed from light gas component and the remainder of the light gas is recycled as stream 65 to the methanation reactor 52. The first hydrogen stream 63 and the naphthalene stream 59 are then fed to a hydrogenation reactor 66 where the naphthalene stream is hydrogenated to produce a tetralin stream 67 comprising 16.4 kg of tetralin. The tetralin stream 67 and the second hydrogen stream 64 are then fed to a hydrocracker 68 where the tetralin is hydrocracked to produce a product stream 69 comprising 3.2 kg benzene, 3.8 kg toluene, 4.4 kg xylenes, 5.5 kg propane and 11.2 kg ethane.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for converting methane to higher hydrocarbons, the process comprising:
   (a) contacting a feed containing methane and at least one of $H_2$, $H_2O$, $CO$ and $CO_2$ with a dehydrocyclization catalyst under conditions effective to convert said methane to aromatic hydrocarbons, including benzene and naphthalene, and produce a first effluent stream comprising aromatic hydrocarbons and hydrogen, wherein said first effluent stream comprises at least 5 wt % more aromatic hydrocarbons than said feed; and
   (b) reacting at least part said aromatic hydrocarbons from said first effluent stream with hydrogen to produce a second effluent stream having a reduced benzene and/or naphthalene content compared with said first effluent stream, wherein said reacting hydrogenates and hydrocracks at least a portion of the naphthalene in said first effluent stream to produce alkylated single ring aromatic compounds.

2. The process of claim 1, wherein at least part of the hydrogen used in (b) is from said first effluent stream.

3. A process for converting methane to higher hydrocarbons and hydrogen, the process comprising:
   (a) contacting a feed containing methane with a dehydrocyclization catalyst under non-oxidizing conditions effective to convert said methane to aromatic hydrocarbons, including benzene and/or naphthalene, and produce a first effluent stream comprising aromatic hydrocarbons and hydrogen, wherein said first effluent stream comprises at least 5 wt % more aromatic hydrocarbons than said feed;

(b) reacting at least part of said aromatic hydrocarbons from said first effluent stream with at least part of the hydrogen from said first effluent stream, said reacting being conducted at a first location and producing a second effluent stream having a reduced benzene and/or naphthalene content compared with said first effluent stream;

(c) transporting at least part of said second effluent stream to a second location remote from said first location; and (d) dehydrogenating at least part of said second effluent stream at said second location to produce hydrogen and a third effluent stream having an enhanced benzene and/or naphthalene content compared with said second effluent stream.

4. The process of claim 3 further comprising reacting at least part of the hydrogen from said first effluent stream with an oxygen containing species to produce a further effluent stream comprising water and hydrocarbon; and recycling at least part of the hydrocarbon in said further effluent stream to said contacting (a).

5. The process of claim 4 wherein said oxygen-containing species comprises carbon monoxide and/or carbon dioxide.

6. The process of claim 5 wherein said oxygen-containing species comprises carbon dioxide introduced to the process as part of a natural gas stream.

7. The process of claim 6 wherein said natural gas stream also contains at least part of the methane in the feed in (a).

8. The process of claim 4 wherein said further effluent stream comprises water and methane, ethane or a mixture of methane and ethane.

9. The process of claim 5 wherein oxygen-containing species comprises carbon monoxide and said further effluent stream comprises one or more of $C_2$ to $C_5$ paraffins and olefins, single-ring aromatic hydrocarbons and $C_1$ to $C_3$ alcohols.

10. The process of claim 4 wherein said reacting at least part of the hydrogen from said first effluent stream with an oxygen containing species includes selective hydrogen combustion.

11. The process of claim 3 wherein said feed in (a) also contains at least one of $H_2$, $H_2O$, CO and $CO_2$.

12. The process of claim 3 wherein said feed in (a) contains less than 5 wt % of $C_3+$ hydrocarbons.

13. The process of claim 1 wherein said conditions in (a) are non-oxidizing conditions.

14. The process of claim 3 wherein said conditions in (a) include a temperature of about 400° C. to about 1200° C., a pressure of about 1 kPa to about 1000 kPa and a weight hourly space velocity of about 0.1 $hr^{-1}$ to about 1000 $hr^{-1}$.

15. The process of claim 3 wherein said dehydrocyclization catalyst in (a) comprises at least one of molybdenum, tungsten, rhenium, a molybdenum compound, a tungsten compound, and a rhenium compound on ZSM-5, silica or an aluminum oxide.

16. The process of claim 1 wherein said reacting (b) hydrocracks at least a portion of the naphthalene or benzene in said first effluent stream to produce normal and isoparaffins.

17. The process of claim 3 and further comprising separating at least one aromatic hydrocarbon from said first effluent stream.

18. The process of claim 17 wherein part of said first effluent stream remaining after separation of at least one aromatic hydrocarbon is used as fuel to provide heat to said contacting (a).

19. The process of claim 3 and further comprising alkylating at least one aromatic hydrocarbon in said first effluent stream with an alkylating agent.

20. The process of claim 19 wherein said alkylating agent comprises ethylene produced in said contacting (a).

21. The process of claim 19 wherein said alkylating agent comprises carbon monoxide and hydrogen or a reaction product thereof.

22. The process of claim 1 further comprising reacting at least part of the hydrogen from said first effluent stream with an oxygen containing species to produce a further effluent stream comprising water and hydrocarbon; and recycling at least part of the hydrocarbon in said further effluent stream to said contacting (a).

23. The process of claim 22 wherein said oxygen-containing species comprises carbon monoxide and/or carbon dioxide.

24. The process of claim 23 wherein said oxygen-containing species comprises carbon dioxide introduced to the process as part of a natural gas stream.

25. The process of claim 24 wherein said natural gas stream also contains at least part of the methane in the feed in (a).

26. The process of claim 22 wherein said further effluent stream comprises water and methane, ethane or a mixture of methane and ethane.

27. The process of claim 22 wherein oxygen-containing species comprises carbon monoxide and said further effluent stream comprises one or more of $C_2$ to $C_5$ paraffins and olefins, single-ring aromatic hydrocarbons and $C_1$ to $C_3$ alcohols.

28. The process of claim 22 wherein said reacting at least part of the hydrogen from said first effluent stream with an oxygen containing species includes selective hydrogen combustion.

29. The process of claim 22 wherein said feed in (a) also contains at least one of $H_2$, $H_2O$, CO and $CO_2$.

30. The process of claim 22 wherein said feed in (a) contains less than 5 wt % of $C_3+$ hydrocarbons.

31. The process of claim 22 wherein said conditions in (a) include a temperature of about 400° C. to about 1200° C., a pressure of about 1 kPa to about 1000 kPa and a weight hourly space velocity of about 0.1 $hr^{-1}$ to about 1000 $hr^{-1}$.

32. The process of claim 22 wherein said dehydrocyclization catalyst in (a) comprises at least one of molybdenum, tungsten, rhenium, a molybdenum compound, a tungsten compound, and a rhenium compound on ZSM-5, silica or an aluminum oxide.

33. The process of claim 22 and further comprising separating at least one aromatic hydrocarbon from said first effluent stream.

34. The process of claim 33 wherein part of said first effluent stream remaining after separation of at least one aromatic hydrocarbon is used as fuel to provide heat to said contacting (a).

35. The process of claim 22 and further comprising alkylating at least one aromatic hydrocarbon in said first effluent stream with an alkylating agent.

36. The process of claim 35 wherein said alkylating agent comprises ethylene produced in said contacting (a).

37. The process of claim 35 wherein said alkylating agent comprises carbon monoxide and hydrogen or a reaction product thereof.

38. A process for converting methane to higher hydrocarbons and hydrogen, the process comprising:

(a) contacting a feed containing methane with a dehydrocyclization catalyst under non-oxidizing conditions effective to convert said methane to aromatic hydrocarbons, including benzene and/or naphthalene, and produce a first effluent stream comprising aromatic hydrocarbons and hydrogen, wherein said first effluent stream comprises at least 5 wt % more aromatic hydrocarbons than said feed;
(b) reacting at least part of said aromatic hydrocarbons from said first effluent stream with at least part of the hydrogen from said first effluent stream, said reacting being conducted at a first location and producing a second effluent stream having a reduced benzene and/or naphthalene content compared with said first effluent stream;
(c) transporting at least part of said second effluent stream to a second location remote from said first location;
(d) dehydrogenating at least part of said second effluent stream at said second location to produce hydrogen and a third effluent stream having an enhanced benzene and/or naphthalene content compared with said second effluent stream; and
(e) reacting at least part of the hydrogen from said first effluent stream with an oxygen containing species to produce a further effluent stream comprising water and hydrocarbon; and recycling at least part of the hydrocarbon in said further effluent stream to said contacting (a).

* * * * *